United States Patent
Orszulak (10) Patent No.: US 8,932,291 B2
(45) Date of Patent: Jan. 13, 2015

(54) ELECTROSURGICAL SYSTEMS

(75) Inventor: James H. Orszulak, Nederland, CO (US)

(73) Assignee: Covidien LP, Mansfield, MA (US)

(*) Notice: Subject to any disclaimer, the term of this patent is extended or adjusted under 35 U.S.C. 154(b) by 412 days.

(21) Appl. No.: 13/446,096

(22) Filed: Apr. 13, 2012

(65) Prior Publication Data

US 2013/0274729 A1 Oct. 17, 2013

(51) Int. Cl.
*A61B 18/18* (2006.01)

(52) U.S. Cl.
USPC .............................................. 606/42

(58) Field of Classification Search
USPC .............................................. 606/42
See application file for complete search history.

(56) References Cited

U.S. PATENT DOCUMENTS

| | | | |
|---|---|---|---|
| 4,188,927 A * | 2/1980 | Harris .............................. | 606/38 |
| 4,438,766 A | 3/1984 | Bowers | |
| 5,443,462 A * | 8/1995 | Hannant ......................... | 606/34 |
| 6,261,286 B1 | 7/2001 | Goble et al. | |
| D574,323 S | 8/2008 | Waaler | |
| 7,551,958 B2 | 6/2009 | Libbus et al. | |
| 7,766,905 B2 | 8/2010 | Paterson et al. | |
| 7,909,820 B2 | 3/2011 | Lipson et al. | |
| 2005/0113820 A1 | 5/2005 | Goble et al. | |
| 2010/0198099 A1 | 8/2010 | Murphy et al. | |
| 2010/0294827 A1 | 11/2010 | Boyden et al. | |

FOREIGN PATENT DOCUMENTS

| | | |
|---|---|---|
| DE | 179607 | 3/1905 |
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |

(Continued)

OTHER PUBLICATIONS

U.S. Appl. No. 10/406,690, filed Apr. 3, 2003, Robert J. Behnke, II.

(Continued)

*Primary Examiner* — George Manuel (57) ABSTRACT

An electrosurgical generator is provided and includes an RF energy output module and an energy request detection module both in communication with one or more processors of the electrosurgical generator. The RF energy module outputting RF energy through a first transformer, and the energy request detection module in electrical communication with primary windings of a second transformer. An electrosurgical instrument is provided and includes a housing, at least one treatment member and one or more switches. The switch is in electrical communication with the first transformer and is coupled to secondary windings of the second transformer such that when the at least one switch is moved to a closed configuration the energy detection module detects an occurrence at the second transformer and provides a signal to the at least one processor to transmit electrosurgical energy to the electrosurgical instrument.

15 Claims, 3 Drawing Sheets

(56) References Cited

FOREIGN PATENT DOCUMENTS

| | | |
|---|---|---|
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4206433 | 9/1993 |
| DE | 4339049 | 5/1995 |
| DE | 19506363 | 8/1996 |
| DE | 19717411 | 11/1998 |
| DE | 19848540 | 5/2000 |
| DE | 10 2008058737 | 4/2010 |
| EP | 246350 | 11/1987 |
| EP | 267403 | 5/1988 |
| EP | 296777 | 12/1988 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 882955 | 12/1998 |
| EP | 1051948 | 11/2000 |
| EP | 1366724 | 1/2006 |
| EP | 880220 | 6/2006 |
| EP | 1776929 | 4/2007 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| JP | 63 005876 | 1/1988 |
| JP | 2002-065690 | 3/2002 |
| SU | 166452 | 1/1965 |
| SU | 727201 | 4/1980 |
| WO | WO02/11634 | 2/2002 |
| WO | WO02/45589 | 6/2002 |
| WO | WO03/090635 | 11/2003 |
| WO | WO2006/050888 | 5/2006 |
| WO | WO2008/053532 | 5/2008 |

OTHER PUBLICATIONS

U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 13/048,639, filed Mar. 15, 2011, James S. Cunningham.
U.S. Appl. No. 13/049,459, filed Mar. 16, 2011, James H. Orszulak.
U.S. Appl. No. 13/050,770, filed Mar. 17, 2011, Robert B. Smith.
U.S. Appl. No. 13/085,258, filed Apr. 12, 2011, Ronald J. Podhajsky.
U.S. Appl. No. 13/085,278, filed Apr. 12, 2011, James A. Gilbert.
U.S. Appl. No. 13/118,973, filed May 31, 2011, James H. Orszulak.
U.S. Appl. No. 13/186,092, filed Jul. 19, 2011, George J. Collins.
U.S. Appl. No. 13/186,107, filed Jul. 19, 2011, George J. Collins.
U.S. Appl. No. 13/186,121, filed Jul. 19, 2011, George J. Collins.
U.S. Appl. No. 13/195,607, filed Aug. 1, 2011, James H. Orszulak.
U.S. Appl. No. 13/221,424, filed Aug. 30, 2011, James E. Krapohl.
U.S. Appl. No. 13/228,996, filed Sep. 9, 2011, Robert B. Smith.
U.S. Appl. No. 13/236,997, filed Sep. 20, 2011, Robert J. Behnke, II.
U.S. Appl. No. 13/237,068, filed Sep. 20, 2011, Robert J. Behnke, II.
U.S. Appl. No. 13/237,187, filed Sep. 20, 2011, Robert J. Behnke, II.
U.S. Appl. No. 13/237,342, filed Sep. 20, 2011, Robert J. Behnke, II.
U.S. Appl. No. 13/237,488, filed Sep. 20, 2011, Robert J. Behnke, II.
U.S. Appl. No. 13/247,043, filed Sep. 28, 2011, Donald W. Heckel.
U.S. Appl. No. 13/358,129, filed Jan. 25, 2012, Joseph D. Brannan.
U.S. Appl. No. 13/360,140, filed Jan. 27, 2012, James E. Krapohl.
U.S. Appl. No. 13/426,204, filed Mar. 21, 2012, Robert B. Smith.
U.S. Appl. No. 13/427,111, filed Mar. 22, 2012, Daniel A. Joseph.
U.S. Appl. No. 13/442,460, filed Apr. 9, 2012, James E. Krapohl.
U.S. Appl. No. 13/446,096, filed Apr. 13, 2012, James H. Orszulak.
U.S. Appl. No. 13/469,960, filed May 11, 2012, Robert J. Behnke, II.
U.S. Appl. No. 13/483,815, filed May 30, 2012, Jeffrey R. Unger.
U.S. Appl. No. 13/485,083, May 31, 2012, Robert J. Behnke, II.
U.S. Appl. No. 13/526,205, filed Jun. 18, 2012, Jeffrey L. Jensen.
U.S. Appl. No. 13/540,347, filed Jul. 2, 2012, Ronald J. Podhajsky.
U.S. Appl. No. 13/593,550, filed Aug. 24, 2012, Ronald J. Podhajsky.
U.S. Appl. No. 13/584,192, filed Aug. 13, 2012, Joseph D. Brannan.
U.S. Appl. No. 13/587,400, filed Aug. 16, 2012, James H. Orszulak.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'". Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51: (1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . " Journal of Applied Sciences-Yingyong Kexue Xuebao, Shangha CN, vol. 23 No. 2;(Mar. 2005); pp. 160-164.

(56) References Cited

OTHER PUBLICATIONS

Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report Ep 07001485.7 dated May 15, 2007.
International Search Report EP 07001489.9 dated Dec. 20, 2007.
International Search Report EP 07001491 dated Jun. 6, 2007.
International Search Report EP 07001494.9 dated Aug. 25, 2010.
International Search Report EP 07001494.9 extended dated Mar. 7, 2011.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report EP09003678.1 dated Aug. 7, 2009.
International Search Report EP09004250.8 dated Aug. 2, 2010.
International Search Report EP09005160.8 dated Aug. 27, 2009.
International Search Report EP09009860 dated Dec. 8, 2009.
International Search Report EP09012386 dated Apr. 1, 2010.
International Search Report EP09012388.6 dated Apr. 13, 2010.
International Search Report EP09012389.4 dated Jul. 6, 2010.
International Search Report EP09012391.0 dated Apr. 19, 2010.
International Search Report EP09012392 dated Mar. 30, 2010.
International Search Report EP09012396 dated Apr. 7, 2010.
International Search Report EP09012400 dated Apr. 7, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP09763515.5 dated Nov. 29, 2011.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report EP10164740.2 dated Aug. 3, 2010.
International Search Report EP10171787.4 dated Nov. 18, 2010.
International Search Report EP10172636.2 dated Dec. 6, 2010.
International Search Report EP10174476.1 dated Nov. 12, 2010.
International Search Report EP10178287.8 dated Dec. 14, 2010.
International Search Report EP10179305.7 dated Aug. 23, 2011.
International Search Report EP10179321.4 dated Mar. 18, 2011.
International Search Report EP10179353.7 dated Dec. 21, 2010.
International Search Report EP10179363.6 dated Jan. 12, 2011.
International Search Report EP10180004.3 dated Jan. 5, 2011.
International Search Report EP10180964.8 dated Dec. 22, 2010.
International Search Report EP10180965.5 dated Jan. 26, 2011.
International Search Report EP10181018.2 dated Jan. 26, 2011.
International Search Report EP10181060.4 dated Jan. 26, 2011.
International Search Report EP10182003.3 dated Dec. 28, 2010.
International Search Report EP10182005.8 dated Jan. 5, 2011.
International Search Report EP10188190.2 dated Nov. 22, 2010.
International Search Report EP10191319.2 dated Feb. 22, 2011.
International Search Report EP10195393.3 dated Apr. 11, 2011.
International Search Report EP11006233.8 dated Feb. 2, 2012.
International Search Report EP11155959.7 dated Jun. 30, 2011.
International Search Report EP11155960.5 dated Jun. 10, 2011.
International Search Report EP11168660 dated Sep. 28, 2011.
International Search Report EP11170959.8 dated Dec. 9, 2011.
International Search Report EP11173562.7 dated Nov. 24, 2011.
International Search Report EP11182150.0 dated Nov. 17, 2011.
International Search Report EP11188798.0 dated Dec. 27, 2011.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.

* cited by examiner

Fig. 1

ELECTROSURGICAL SYSTEMS

BACKGROUND

1. Technical Field

The present disclosure relates to electrosurgical systems. More particularly, the present disclosure relates to electrosurgical systems that include an electrosurgical energy request apparatus with non-energized switching capabilities.

2. Description of Related Art

Electrosurgical systems that utilize electrosurgical instruments, typically, include energized energy request apparatuses (e.g., one or more switching devices) that are configured to send energy requests to an electrosurgical generator that is configured to supply electrosurgical energy to the electrosurgical instrument. In certain instances, and for convenience, the switching devices are, typically, operably disposed on the electrosurgical instrument.

One drawback, however, with providing the switching device on the electrosurgical instrument is "RF creepage" breakdown, which is caused as a result of the switching devices being located within the electrosurgical instrument and in close proximity to the electrosurgical energy provided to the electrosurgical instrument. To reduce or eliminate this "RF creepage" breakdown, the switching devices are, typically, provided with one or more isolated power sources and detection circuits; this, however, increases the potential for alternate RF leakage paths during operation at elevated RF levels. Diverted RF energy through the switching device and/or the RF leakage paths may reduce clinical efficacy and/or may create a non-desirable environment for a patient.

Another potential drawback, with diverting the RF energy through the switching device is a potential for switch "burnout." To compensate for this switch "burnout" one or more additional isolation components are, typically, placed in series with the switching device.

SUMMARY

In view of the foregoing, it may prove advantageous in the medical art to provide electrosurgical systems that include an electrosurgical energy request apparatus with non-energized switching capabilities.

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

An aspect of the present disclosure provides an electrosurgical system. The electrosurgical system includes an electrosurgical generator including an RF energy output module and an energy request detection module. Each of the RF energy output module and energy request module is in communication with at least one processor of the electrosurgical generator. The RF energy module outputting RF energy through a first transformer and the energy request detection module is in electrical communication with primary windings of a second transformer. The electrosurgical system includes an electrosurgical instrument having a housing, a treatment member and at least one switch. The at least one switch is in electrical communication with the first transformer and is coupled to secondary windings of the second transformer such that when the at least one switch is moved to a closed configuration the energy detection module detects an occurrence at the second transformer and provides a signal to the at least one processor to transmit electrosurgical energy to the electrosurgical instrument.

In certain instances, the second transformer may be either a magnetic core or air core transformer.

The at least one switch may be in a normally open configuration.

In certain instances, a high inductive impedance may be present on the primary windings of the second transformer when the at least one switch is in the normally open configuration and a low inductive impedance may be present on the primary windings of the second transformer when the at least one switch is in a closed configuration.

In one instances, the occurrence detected by the energy request detection block may be inductive impedance.

Under certain surgical scenarios, it may prove advantageous for the electrosurgical instrument to be configured to function in more than one mode of operation. In this instance, the electrosurgical system may further include a second switch, and a third transformer that is connected in parallel relation with respect to the second transformer and includes secondary windings connected to the at least second switch. Each of the primary windings of the second and third transformers may include a respective resistor connected in series therewith. Resistance values may be different for each of the respective resistors and may be correlated to a specific one of the at least two switches to indicate to the at least one processor which of the at least two switches is closed.

In certain instances, the resistance values are different for each of the respective resistors to provide unique oscillation frequencies that are correlated to a specific one of the at least two switches to indicate to the at least one processor which of the at least two switches is closed. In this particular instance, the occurrence detected by the energy request detection block is an oscillator frequency of the respective resistors.

In certain instances, each of the primary windings of the second and third transformers includes a respective capacitor connected in series therewith. In this instance, capacitance values are different for each of the respective capacitors to provide unique resonant tank periods that are correlated to a specific one of the at least two switches to indicate to the at least one processor which of the at least two switches is closed. In this particular instance, the occurrence detected by the energy request detection block is a resonant tank period of the primary windings of the second and third transformers and the respective capacitors.

In certain instances it may prove advantageous to connect at least one of the secondary windings of the second transformer to one of the secondary windings of the first transformer. In this instance, at least one of the secondary windings of the second transformer is connected to at least one lead that provides electrosurgical energy to one of the first and second jaw members.

In certain instances it may prove advantageous to connect both of the secondary windings of the second transformer to one of the secondary windings of the first transformer.

In one particular instance, at least one of the secondary windings of the second transformer is in electrical communication with the at least one switch via a lead that is part of a cable that couples the electrosurgical instrument to the electrosurgical generator.

In some instances, the at least one switch may either be a handswitch that is operably disposed on the electrosurgical instrument or a footswitch that is in operable communication with the electrosurgical generator.

An aspect of the present disclosure provides an electrosurgical system that includes an electrosurgical generator including an energy request detection module in communication with at least one processor of the electrosurgical generator. The energy request detection module is in electrical communication with an isolation transformer of the electrosurgical generator. The electrosurgical system includes an electrosurgical instrument including at least one treatment member and at least one switch. The at least one switch is in electrical communication with the isolation transformer such that when the at least one switch is moved to a closed configuration the energy detection module detects an occurrence at the isolation transformer and provides a signal to the at least one processor to transmit electrosurgical energy to the electrosurgical instrument.

BRIEF DESCRIPTION OF THE DRAWING

Various embodiments of the present disclosure are described hereinbelow with references to the drawings, wherein.

DETAILED DESCRIPTION

To overcome some of the aforementioned drawbacks, the present disclosure provides a unique electrosurgical system with non-energized switching capabilities. In particular, one or more isolating transformers are electrically coupled to one or more switches disposed on an electrosurgical instrument of the electrosurgical system to provide an energy activation signal to one or more processors of the electrosurgical system.

Figure 1:
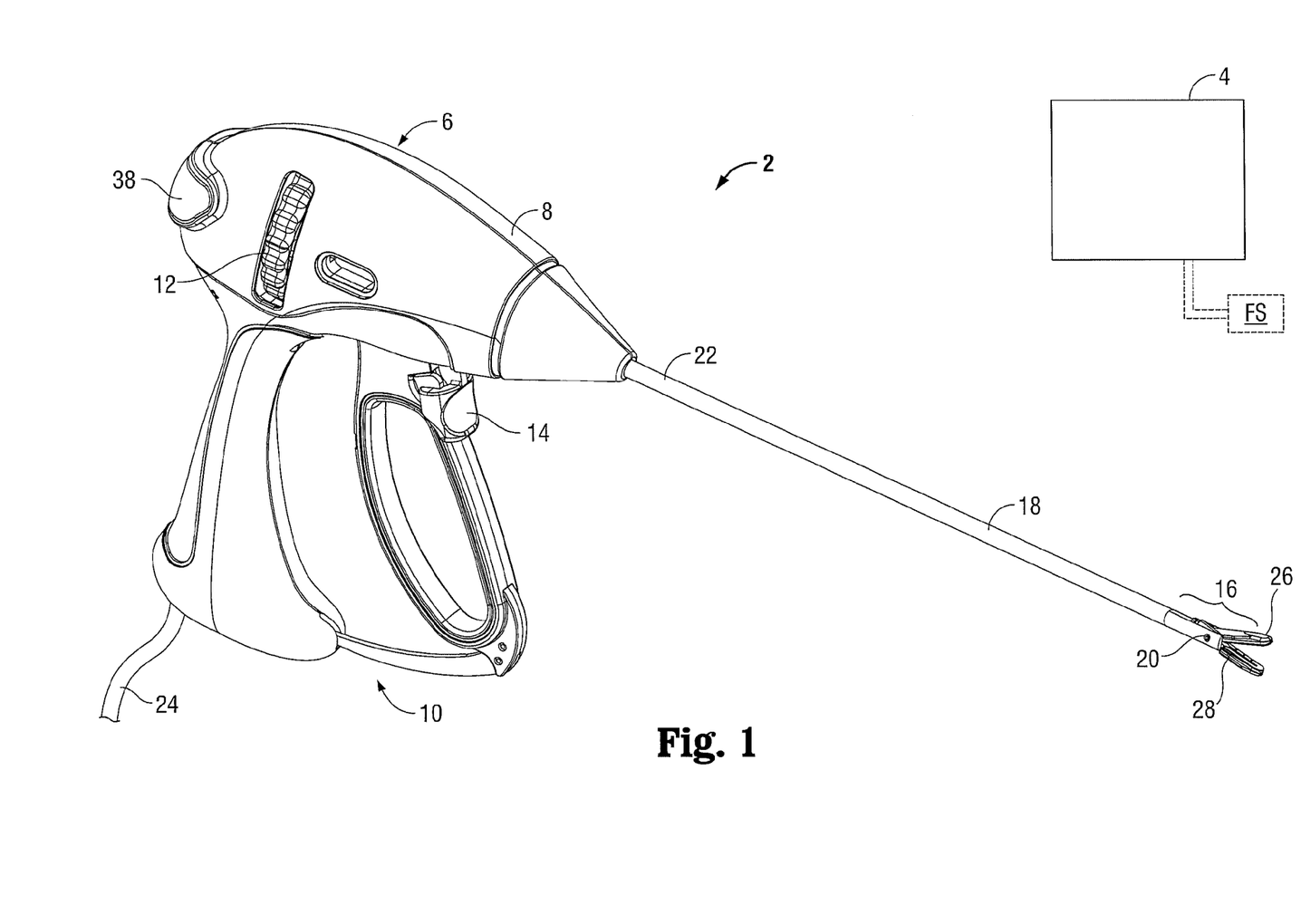
FIG. 1 is a perspective view of an electrosurgical system according to an embodiment of the present disclosure.

Turning now to FIG. 1, an electrosurgical system 2 is illustrated including a generator 4 and an electrosurgical device such as, for example, an electrosurgical forceps configured for use in open or closed laparoscopic procedures. For illustrative purposes, FIG. 1 shows an endoscopic electrosurgical forceps 6 that is configured for laparoscopic procedures and includes a housing 8, a handle assembly 10, a rotating assembly 12, a trigger assembly 14 and an end effector assembly 16. Forceps 6 further includes a shaft 18 having a distal end 20 configured to mechanically engage end effector assembly 16 and a proximal end 22 that mechanically engages housing 8. Forceps 6 also includes electrosurgical cable 24 that connects forceps 6 to the generator 4 or other suitable power source. Cable 24 includes a lead (or leads) 24a-24c (FIG. 2) extending therethrough that has sufficient length to extend through shaft 22 in order to provide electrical energy to one or more treatment members, e.g., a pair of jaw members 26 and 28, of the end effector assembly 16. Forceps 6 may be configured for bipolar (both jaw members 26 and 28 are conductive) or monopolar modes of operation. In the latter instance, one of the jaw members 26 and 28 are conductive and a return pad (not explicitly shown) is configured to function as a return electrode.

Figure 2:
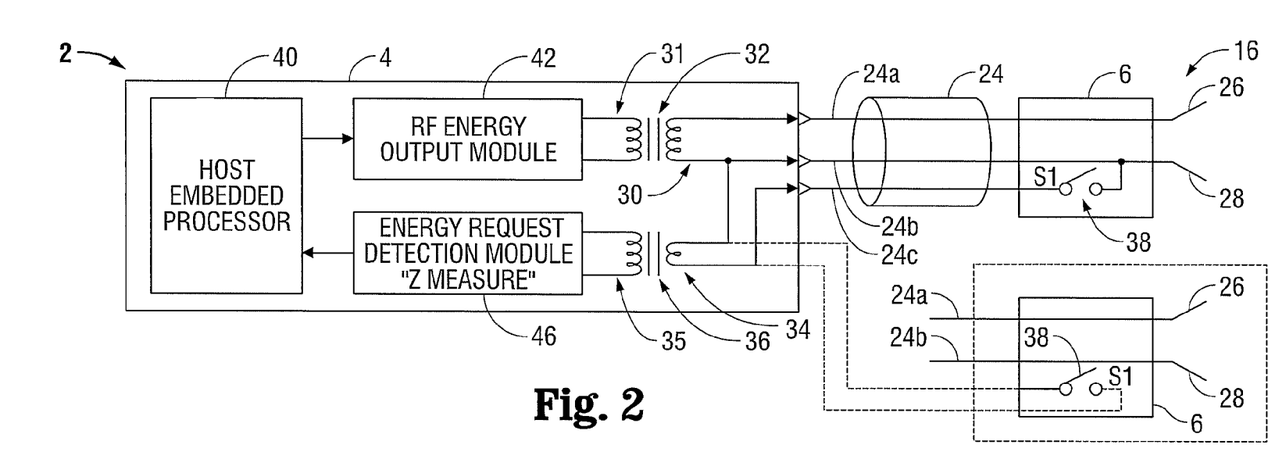
FIG. 2 is schematic plan view of the electrosurgical system depicted in FIG. 1.

Referring to FIGS. 1 and 2, cable 24 includes leads 24a-24c. When coupled to the generator 4, leads 24a and 24b connect to a pair of secondary windings 30 of a first transformer 32 (patient isolation transformer) operably associated with the generator 4. Leads 24a-24b provide a path for an output of the patient isolation transformer 32 to the jaw members 26 and 28 (FIG. 2). When coupled to the generator 4, lead 24c connects one leg of a pair of secondary windings 34 of a second transformer 36 (isolation transformer) to a switch 38 on the forceps 6 (FIG. 2).

Continuing with reference to FIG. 2, generator 4 includes one or more processors 40, an RF energy output module 42 (output module 42) that communicates with the patient isolation transformer 32, and an energy request detection module 46 (detection module 46) that communicates with the isolation transformer 36.

Processor 40 is in operable communication with each of the output module 42 and detection module 46 (FIG. 2). In particular, when the switch 38 is activated, the processor 40 receives a recognition signal from the detection module 46 to signal an activation request for RF energy from the output module 42 to the forceps 6.

Patient isolation transformer 32 (FIG. 2) receives the RF energy at its primary windings 31 from the output module 42 and outputs the RF energy from its secondary windings 32 through the leads 24a and 24b of the cable 24 to jaw members 26 and 28 of the forceps 6 to electrosurgically treat tissue, e.g., seal tissue. Patient isolation transformer 32 may be any suitable type of transformer. In the illustrated embodiments, patient isolation transformer 32 may be a magnetic core transformer.

Isolation transformer 36 (FIG. 2) is in electrical communication with each of the switch 38 and the detection module 46. In particular, isolation transformer 36 includes primary windings 35 that are coupled to the detection module 46 and secondary windings 34 that are coupled to the secondary windings 30 of the patient isolation transformer 32 and the switch 38. Coupling the secondary windings 34 of the isolation transformer 36 in this manner provides an increased benefit to create an impedance block to the flow of RF energy through the switch 38, which, in turn, may increase activation reliability of switch 38.

With reference again to FIG. 2, switch 38 is in electrical communication with the patient isolation transformer 32 and is coupled to secondary windings 34 of the isolation transformer 36. Switch 38 may be any suitable type of switch. In the illustrated embodiments, the switch 38 is a handswitch of the push-button type that is located on the forceps 6. Switch 38 is configured to function in a normally open configuration. In the normally open configuration, one of the contacts of the switch 38 is electrically connected to the lead 24b (see FIG. 2 for example) and nominally high inductive impedance is present at the primary windings 35 of the isolation transformer 36. When the switch 38 is moved to a closed configuration, both of the contacts of the switch 38 are electrically connected to the lead 24b (not explicitly shown) and low inductive impedance is present at the primary windings 35. That is, moving the switch 38 to a closed configuration essentially "shorts" the isolation transformer 36, e.g., moving the switch 38 to a closed configuration provides a path for "leakage inductance."

When the switch 38 is moved to a closed configuration, the detection module 46 is configured to detect one or more occurrences at the isolation transformer 36 and to provide a signal to the processor 40 to transmit electrosurgical energy to the forceps 6 (FIG. 2). In accordance with the instant disclosure, the detection module 46 can be configured to detect occurrences at the isolation transformer 36 that include, but are not limited to, a specific impedance, such as, for example, resistive impedance, inductive impedance, capacitive impedance, etc. (FIGS. 2 and 3), a specific oscillator frequency (FIG. 4), a specific resonant pulse period (FIG. 5), a specific power output, a specific temperature, a specific current, a specific voltage, etc. For example, and with specific reference to FIG. 2, a change in inductive impedance corresponds to an occurrence at the primary windings 35 and is detected by the detection module 46. This change in inductive impedance correlates to the switch 38 being in a closed configuration.

In use, with switch 38, initially, in a normally open configuration, tissue is positioned between jaw members 26 and 28; nominally high inductive impedance is present at the primary windings 35 of the isolation transformer 36. Subsequently, jaw members 26 and 28 are approximated toward one another to grasp tissue. Thereafter, switch 38 is depressed generating a closed circuit across the secondary windings 34 of the isolation transformer 36, and thus, short circuiting the isolation transformer 36. Shorting the isolation transformer changes a nominally high inductive impedance at the primary windings 35 to a relatively low inductive impedance at the primary windings 35.

Detection module 46 detects this change in inductive impedance and outputs a signal to the processor 40 to drive the output module 42 for transmission of RF energy to the jaw members 26 and 28 of the forceps 6 to electrosurgically treat tissue, e.g. seal tissue.

During transmission of RF energy to the jaw members 26 and 28, the unique configuration of the switch 38 and isolation transformer 36 in communication with the detection module 46 overcomes the drawbacks of the aforementioned conventional forceps. In particular, the need for isolated power sources and isolated detection circuits that are, typically, utilized with conventional forceps is eliminated. As a result thereof, RF energy delivery is increased to the surgical site by reducing alternate energy leakage paths that are associated with the isolated power sources and isolated detection circuits. Moreover, intrinsically high inductive reactance of the secondary windings 34 creates a "blocking impedance" to the flow of RF energy through the switch 38 when the switch 38 is in the closed configuration. This reduces and/or eliminates, the likelihood of the switch 38 burning out (switch burnout) and, thus, increases switch activation reliability of the switch 38. Further, the configuration of the switch 38 and isolation transformer 36 provides a high isolation, non-energized energy request switching means thereby increasing patient safety.

Figure 3:
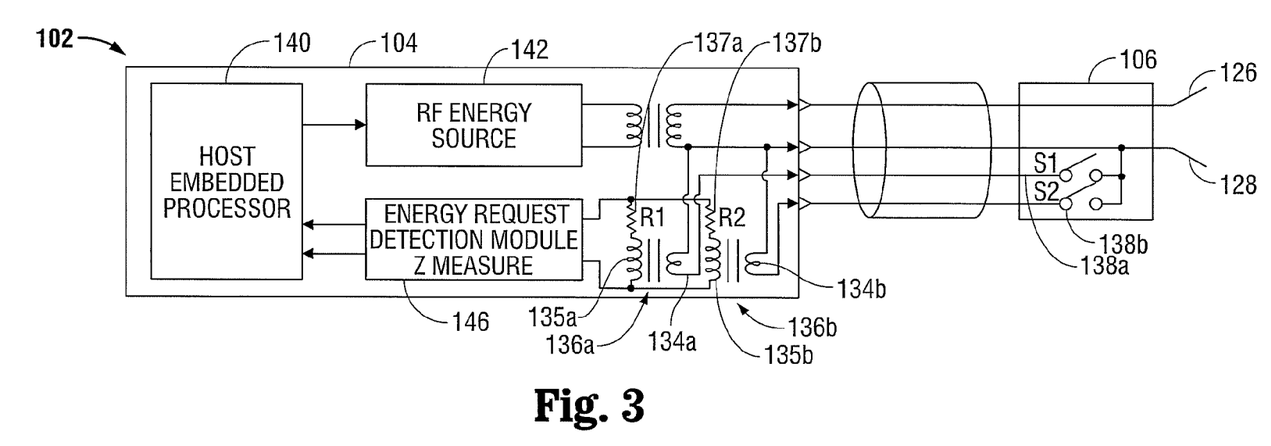
FIG. 3 is schematic plan view of an electrosurgical system according to another embodiment of the present disclosure.

With reference to FIG. 3, an electrosurgical system 102 that utilizes non-energized switching capabilities according to another embodiment of the present disclosure is shown. Electrosurgical system 102 and operative components associated therewith is substantially similar to electrosurgical system 2. Accordingly, only those features unique to electrosurgical system 102 are described herein.

In the embodiment illustrated in FIG. 3, the electrosurgical system 102 includes a generator 104 and forceps 106 that are configured to function in one more treatment protocols, e.g., a seal mode of operation and one or more other modes of operation, e.g., coagulation mode of operation, desiccation mode of operation, fulguration mode of operation, etc. In the embodiment illustrated in FIG. 3, the second mode of operation is a coagulation mode of operation. To this end, electrosurgical system 102 includes a switch 138a that is coupled to patient isolation transformer 136a and, unlike electrosurgical system 2, includes a second switch 138b that is coupled to a second isolation transformer 136b.

Isolation transformers 136a and 136b are coupled in a parallel configuration and include respective resistors 137a and 137b that are coupled in series to the primary windings 135a and 135b. The resistance value of the resistors 137a and 137b creates a unique impedance (or range of impedance) that correlates to the respective switches 138a and 138b being in the closed configuration.

Processor 140 is configured to receive and/or detect the impedance across primary windings 135a and resistor 137a, and across primary windings 135b and resistor 137b. This impedance across the primary windings 135a and resistor 137a correlates to switch 138a being in the closed configuration. Likewise, impedance across the primary windings 135b and resistor 137b correlates to switch 138b being in the closed configuration. In the embodiment illustrated in FIG. 3, switch 138a in the closed configuration corresponds to a seal mode of operation. Similarly, switch 138b in the closed configuration corresponds to a coagulation mode of operation.

In use, with switches 138a and 138b, initially, in a normally open configuration, tissue is positioned between jaw members 126 and 128; nominally high inductive impedance is present at the primary windings 135a and 135b of the respective isolation transformers 136a and 136b. Subsequently, jaw members 126 and 128 are approximated toward one another to grasp tissue. Thereafter, either switch 138a or 138b is depressed generating a closed circuit across either of the secondary windings 134a and 134b of the respective isolation transformers 136a and 136b, and thus, short circuiting the isolation transformers 136a and 136b. Shorting either of the isolation transformers 136a and 136b changes a nominally high inductive impedance at the primary windings 135a and 135b to a relatively low inductive impedance at the primary windings 135a and 135b. Unlike isolation transformer 36 of FIG. 2, however, depending which switch 138a and 138b is depressed a resistance is present across primary windings 135a and resistor 137a, or across primary windings 135b and resistor 137b.

Detection module 146 detects this resistance and outputs a signal to the processor 140 to drive the output module 142 for transmission of RF energy to the jaw members 126 and 128 of the forceps 6 to electrosurgically treat tissue, e.g., either seal or coagulate tissue.

Figure 4:
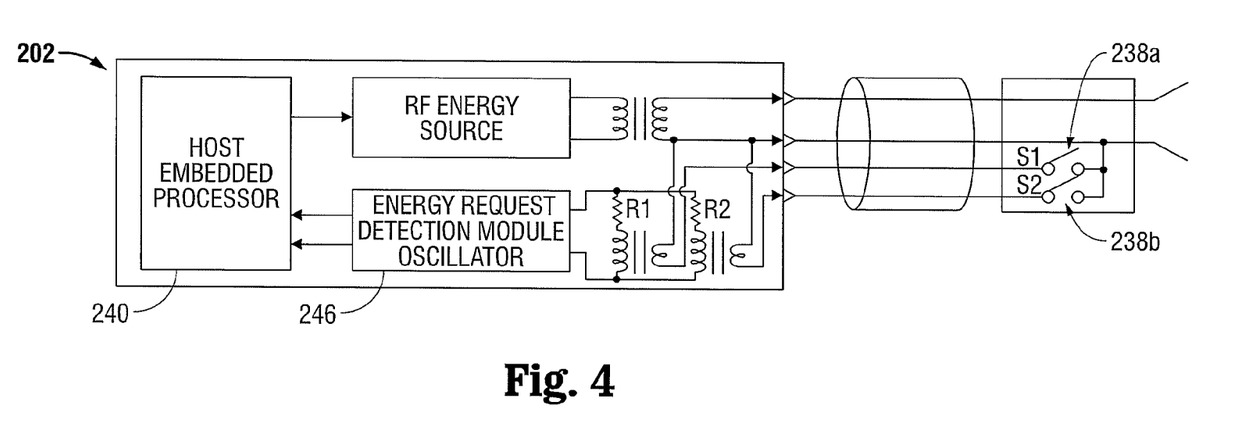
FIG. 4 is schematic plan view of an electrosurgical system according to yet another embodiment of the present disclosure.

With reference to FIG. 4, an electrosurgical system 202 that utilizes non-energized switching capabilities according to another embodiment of the present disclosure is shown. Electrosurgical system 202 and operative components associated therewith is substantially similar to electrosurgical system 102. Accordingly, only those features unique to electrosurgical system 202 are described herein.

Unlike detection module 46, detection module 246 is configured to detect a unique oscillator frequency that is correlated to the closure of switches 238a and 238b. In this embodiment, the detection module 246 transmits the individual oscillator frequency to the processor 240 that implements frequency discriminator decoding to correlate the desired treatment protocol, e.g., seal or coagulation mode of operation. Other than utilizing a unique oscillator frequency, electrosurgical system 202 operates identical to that of electrosurgical system 102. Accordingly, operation of the electrosurgical system 202 is not described in further detail.

Figure 5:
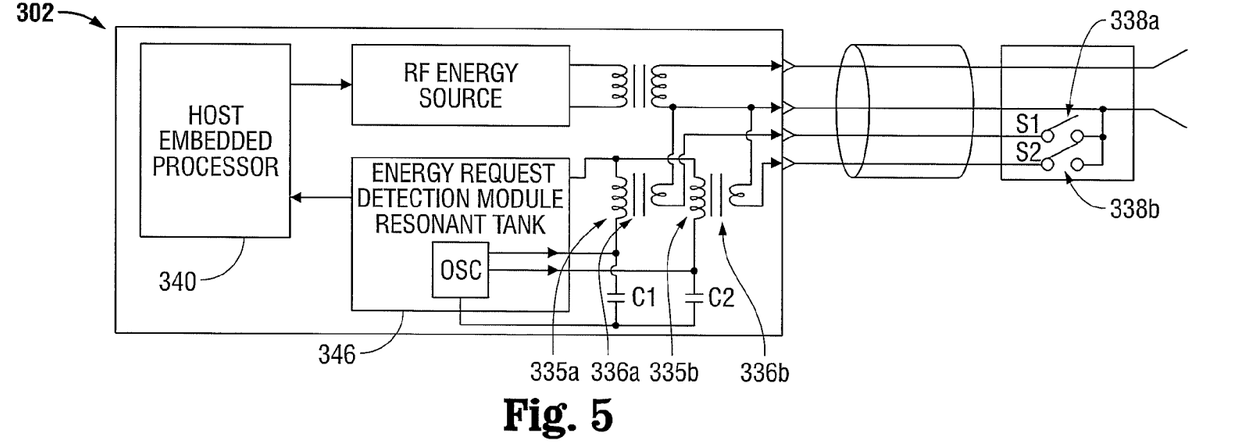
FIG. 5 is schematic plan view of an electrosurgical system according to still another embodiment of the present disclosure.

With reference to FIG. 5, an electrosurgical system 302 that utilizes non-energized switching capabilities according to another embodiment of the present disclosure is shown. Electrosurgical system 302 and operative components associated therewith is substantially similar to the aforementioned electrosurgical systems 2, 102 and 202. Accordingly, only those features unique to electrosurgical system 302 are described herein.

In the embodiment illustrated in FIG. 5, capacitive elements C1 and C2 are connected in series with respective primary windings 335a and 335b to create a unique resonant tank period that is determined by the capacitance of C1 or C2 when the respective switches 338a and 338b are in the closed configuration. In this instance, an internal asynchronous oscillator "OSC" is configured to generate a repetitive pulse train of a given frequency to synchronously drive a nodal connection of each respective isolating transformer 336a and 336b. Moreover, the detection block 346 transmits the individual resonant pulse period to the processor 340 that implements pulse width discriminator decoding to correlate the desired treatment protocol, e.g., seal or coagulation mode of operation. Other than utilizing a unique resonant tank period, electrosurgical system 302 operates identical to that of electrosurgical systems 102 and 202. Accordingly, operation of the electrosurgical system 302 is not described in further detail.

From the foregoing and with reference to the various figure drawings, those skilled in the art will appreciate that certain modifications can also be made to the present disclosure without departing from the scope of the same. For example, while the switch 38 has been described in terms of a handswitch of the push-button type that is disposed on the forceps 6, other types of switches may be utilized. For example, and in one particular embodiment, a footswitch "FS" (shown in phantom in FIG. 1) may be utilized instead of the handswitch. In this instance, the footswitch "FS" may be of the push-button type and may be operably coupled to the generator 4 via a cable (similar to that of cable 24). As can be appreciated, the footswitch "FS," other than the placement of the footswitch "FS" with respect to an end user, is configured to function in a manner as described above with respect to the switch 38.

Further, any of the aforementioned switches, e.g., switch 38, may be "two-wire returned" to the isolation transformer, e.g., isolation transformer 34. FIG. 1 illustrates this "two-wire returned" switch configuration in phantom. In this instance, the switch 38 is isolated from elevated RF levels. This configuration of the switch 38 provides a double insulated boundary at non-elevated RF levels magnetic or air core transformer 36 coupling to further increase patient safety and increase energy delivery to the surgical site by reducing alternate energy leakage paths.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical system, comprising:
   an electrosurgical generator including an RF energy output module and an energy request detection module both in communication with at least one processor of the electrosurgical generator, the RF energy output module outputting RF energy through a first transformer, and the energy request detection module in electrical communication with primary windings of a second transformer; and
   an electrosurgical instrument configured to function in at least two modes of operation and including a housing, a treatment member and at least a first switch and a second switch, the first switch in electrical communication with the first transformer and coupled to secondary windings of the second transformer such that when the first switch is moved to a closed configuration the energy detection module detects an occurrence at the second transformer and provides a signal to the at least one processor to transmit electrosurgical energy to the electrosurgical instrument.

2. An electrosurgical system according to claim 1, wherein the second transformer is one of a magnetic core or an air core transformer.

3. An electrosurgical system according to claim 1, wherein the first switch is in a normally open configuration.

4. An electrosurgical system according to claim 3, wherein a high inductive impedance is present on the primary windings of the second transformer when the first switch is in the normally open configuration and a low inductive impedance is present on the primary windings of the second transformer when the first switch is in a closed configuration.

5. An electrosurgical system according to claim 4, wherein the occurrence detected by the energy request detection module is impedance.

6. An electrosurgical system according to claim 1, further comprising a third transformer that is connected in parallel relation with respect to the second transformer and includes secondary windings connected to the second switch.

7. An electrosurgical system according to claim 6, wherein each of the primary windings of the second and third transformers includes a respective resistor connected in series therewith.

8. An electrosurgical system according to claim 7, wherein resistance values are different for each of the respective resistors and are correlated to a specific one of the first or second switches to indicate to the at least one processor which of the first or second switches is closed.

9. An electrosurgical system according to claim 7, wherein resistance values are different for each of the respective resistors to provide unique oscillation frequencies that are correlated to a specific one of the first or second switches to indicate to the at least one processor which of the first or second switches is closed, the occurrence detected by the energy request detection module corresponding to an oscillator frequency of the respective resistors.

10. An electrosurgical system according to claim 6, wherein each of the primary windings of the second and third transformers includes a respective capacitor connected in series therewith.

11. An electrosurgical system according to claim 10, wherein capacitance values are different for each of the respective capacitors to provide unique resonant tank periods that are correlated to a specific one of the first or second switches to indicate to the at least one processor which of the first or second switches is closed, the occurrence detected by the energy request detection module corresponding to a resonant tank period of the primary windings of the second and third transformers and the respective capacitors.

12. An electrosurgical system according to claim 1, wherein both of the secondary windings of the second transformer are connected to one of the secondary windings of the first transformer.

13. An electrosurgical system forceps according to claim 1, wherein at least one of the secondary windings of the second transformer is in electrical communication with the first switch via a lead that is part of a cable that couples the electrosurgical instrument to the electrosurgical generator.

14. An electrosurgical system according to claim 1, wherein the first switch is one of a handswitch switch operably disposed on the electrosurgical instrument and a footswitch in operable communication with the electrosurgical generator.

15. An electrosurgical system, comprising:
   an electrosurgical generator including an RF energy output module and an energy request detection module both in communication with at least one processor of the electrosurgical generator, the RF energy output module outputting RF energy through a first transformer, and the energy request detection module in electrical communication with primary windings of a second transformer; and
   an electrosurgical instrument including a housing, a treatment member and at least one switch, the at least one switch in electrical communication with the first transformer and coupled to secondary windings of the second transformer such that when the at least one switch is moved to a closed configuration the energy detection module detects an occurrence at the second transformer and provides a signal to the at least one processor to transmit electrosurgical energy to the electrosurgical instrument,
   wherein at least one of the secondary windings of the second transformer is connected to one of the secondary windings of the first transformer and at least one of the secondary windings of the second transformer is connected to at least one lead that provides electrosurgical energy to one of a first or second jaw member of the electrosurgical instrument.

* * * * *